United States Patent
Gumbrecht et al.

(10) Patent No.: US 8,597,574 B2
(45) Date of Patent: Dec. 3, 2013

(54) ANALYSIS DEVICE

(75) Inventors: Walter Gumbrecht, Herzogenaurach (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1491 days.

(21) Appl. No.: 10/471,166

(22) PCT Filed: Mar. 8, 2002

(86) PCT No.: PCT/DE02/00837
§ 371 (c)(1), (2), (4) Date: Sep. 9, 2003

(87) PCT Pub. No.: WO02/072262
PCT Pub. Date: Sep. 19, 2002

(65) Prior Publication Data
US 2004/0115094 A1 Jun. 17, 2004

(30) Foreign Application Priority Data
Mar. 9, 2001 (DE) .................. 101 11 457

(51) Int. Cl.
*G01N 27/00* (2006.01)
(52) U.S. Cl.
USPC .............. 422/82.01; 422/82.04; 422/502; 422/503
(58) Field of Classification Search
USPC ......... 73/1.01, 1.02; 422/50, 56, 57, 58, 68.1, 422/100, 502–507, 401–404, 81–82.09; 436/43, 63, 66, 86
See application file for complete search history.

(56) References Cited

U.S. PATENT DOCUMENTS

| | | | |
|---|---|---|---|
| 4,301,414 A | 11/1981 | Hill et al. | |
| 4,654,127 A | 3/1987 | Baker et al. | |
| 5,096,669 A | 3/1992 | Lauks et al. | |
| 5,405,510 A * | 4/1995 | Betts et al. | 205/782 |
| 5,587,128 A * | 12/1996 | Wilding et al. | 422/50 |
| 5,637,469 A * | 6/1997 | Wilding et al. | 435/7.21 |
| 6,054,277 A * | 4/2000 | Furcht et al. | 435/6 |
| 2002/0196435 A1* | 12/2002 | Cohen et al. | 356/246 |

FOREIGN PATENT DOCUMENTS

| | | |
|---|---|---|
| DE | 195 46 535 | 6/1997 |
| DE | 199 03 705 | 7/2000 |
| GB | 2 224 356 | 5/1990 |
| JP | 2243952 | 9/1990 |
| JP | 3223674 | 10/1991 |
| JP | 4-501768 | 3/1992 |
| JP | 9061311 | 3/1997 |
| JP | 10026625 | 1/1998 |
| WO | 00/52457 | 9/2000 |

OTHER PUBLICATIONS

Dirks, G., "Development of a Disposable Biosensor Chipcard System", MESA Research Institute, pp. 207-212.
Japanese Office Action dated Feb. 28, 2008 for corresponding Japanese Patent Application No. 2002-571214.

* cited by examiner

*Primary Examiner* — Jan Ludlow
(74) *Attorney, Agent, or Firm* — Staas & Halsey LLP

(57) ABSTRACT

A microfluidic diagnosis kit used in biochemical analysis obtains a premeasured amount of reagents in an applicator for an analysis system. The required reagents are proportioned as non-volatile agents and a microfluidic system is provided, whereby the reagents are automatically dissolved in a solvent and fed to a sensor module to carry out measurement.

36 Claims, 4 Drawing Sheets

ANALYSIS DEVICE

CROSS REFERENCE TO RELATED APPLICATIONS

This application is based on and hereby claims priority to German Application No. 101 11 457.5 filed on Mar. 9, 2001, the contents of which are hereby incorporated by reference. This application is related to MODULE FOR AN ANALYSIS DEVICE, APPLICATOR AS AN EXCHANGE PART OF THE ANALYSIS DEVICE AND ANALYSIS DEVICE ASSOCIATED THEREWITH, filed concurrently by Walter Gumbrecht, Manfred Stanzel, Manfred Wossler and Jörg Zapf and incorporated by reference herein.

BACKGROUND OF THE INVENTION

1. Field of the Invention

The invention relates to an analysis device for use in biochemical analytics, with an applicator for decentralized use, containing a first housing, a fluidic system and a sensor module, which together with a second housing forms a measuring and analysis system.

2. Description of the Related Art

One of the requirements for the decentralization of chemical-biological analyses in medical technology is that reagents are flexibly available. In the present context, decentralized means that the analyses are carried out, often not with a high throughput, as in large-scale clinical laboratories. Reagents for chemical-biological analysis are often very costly and greatly restricted in their service life/usability, at least after the container has been opened, for example outgassing of $O_2$ and $CO_2$ from blood-gas calibrating solutions or decomposition of biochemical components, so that efficient, low-cost use is made more difficult or impossible.

Decentralized analyses are therefore carried out particularly advantageously with so-called disposable kits, in which the reagents are provided in a pre-apportioned, individually packed amount required for the specific instance. Known for example is a system (i-STAT Corporation, 303A College Road East, Princeton, N.J. 08540; U.S. Pat. No. 5,096,669) in which a calibrating solution required for the calibration of blood-gas/electrolyte sensors is stored in a gastight aluminum/plastic bag with a content of <1 ml for a disposable sensor and is opened during operation of the disposable sensor by "piercing" the bag wall.

Such a concept of providing calibrating solutions is not suitable for the use of reagents which in dissolved form are subjected to a decomposing process, such as for example enzymes, sensitive organic substances, such as in particular p-aminophenyl-phosphate, p-aminophenyl-β-galactoside. This procedure is also complex and expensive, and there is also the risk of the bags leaking and consequently the entire diagnosis of the blood gas analysis being falsified, for example by escaping gases. Furthermore, in the case of the prior art, only a single calibrating solution is realized and consequently only a one-point calibration is made possible, which casts doubt on the reliability of the results and consequently reduces the acceptance among customers. Although the theoretical possibility of providing more than one calibrating solution is mentioned in U.S. Pat. No. 5,096,669 A, this would increase the complexity, and consequently the production costs, of the disposable article.

Furthermore, the possibility of admixing dry reagents with the sample, i.e. for example the blood sample, is mentioned in U.S. Pat. No. 5,096,669 A. However, this does not solve the problems involved in providing reagents when, for complex diagnostic operations, a number of reagent solutions have to be passed over a sensor device, for example a sensor chip or sensor module, in series before and/or after entry of the sample fluid, for example in the case of analyses with the aid of so-called enzymatic amplification: this involves sequentially feeding in 1. buffer solution, 2. sample, 3. buffer solution, 4. enzyme label reagent, 5. buffer solution, 6. enzyme substrate.

Furthermore, in Dirks, G. et al. "Development of a disposable biosensor chipcard system", Sens. Technol. Neth., Proc. Dutch Sens. Conf, 3rd (1988), pages 207 to 212, there is a description of a measuring system for biomedical applications in which a so-called chip card is made from a flat container with a number of cavities and a system of fluid channels, with an ISFET which serves as a sensor being introduced into the channel system. In the case of this system, it is in particular a matter of separately feeding a measuring fluid on the one hand and a calibrating or reagent fluid on the other hand to the sensor from separate containers.

Furthermore, in the monograph by Langereis, G.R. "An integrated sensor system for monitoring washing process", ISBN 90, there is a description of systems with sensors concerned with integrating in fluidic devices sensors which have their signals electrically tapped.

SUMMARY OF THE INVENTION

The problems of feeding in reagents are not satisfactorily solved in the prior art. On the basis of the prior art, it is therefore an object of the invention to improve an analysis device of the type stated at the beginning for decentralized use.

In the case of the invention, the reagents are kept as solid substances in a pre-portioned form in a microfluidic system in the applicator and, in combination with a suitable operating mode, are automatically dissolved and fed to the analysis system, in particular from a single solvent reservoir for at least one complete analyzing operation, in a number of partial steps. The reagent solutions are consequently produced 'in situ' in the fed-in solvent and are provided only immediately before they are to be used.

By contrast with the prior art—the invention advantageously achieves a technical realization of a number of reagent solutions from just one solvent reservoir for at least one analyzing operation. In the case of the prior art, and specifically in U.S. Pat. No. 5,096,669 A, it is not stated whether, and in particular how, a number of different reagent solutions could be sequentially provided from dry reagents.

In the case of the invention, the reagents are preferably kept in solid form or dissolved in a solid adjuvant, for example water-soluble polymer. An example is the provision of means for prescribing a defined $pCO_2$ value for medical diagnostics: for this purpose, apart from the salts required, such as, inter alia, NaCl and KCl, a solid base substance, for example NaHCO3, and a solid acid substance, for example citric acid, are also introduced. During the dissolving of the reagents, the solid base substance and solid acid substance react, as known in the prior art for example from effervescent tablets, and produce a defined amount of $CO_2$. Since significantly smaller concentrations than in the case of effervescent tablets are required, no formation of bubbles occurs.

Furthermore, the provision of a number of reagent solutions for complex analyzing operations is possible. An advantageous example is an immunoassay with enzymatic amplification. In this case, a washing step with a buffer solution may have to be performed after the sample fluid has been applied to the sensor or sensor module. This may take place either directly from the reservoir or advantageously by dissolving solid buffer substance, for example dissolved in water-soluble polymer and placed in a micro-throughflow channel from a water reservoir, which may be placed in the applicator or in the second housing. This is followed by enzyme label being fed in, to be precise advantageously likewise placed as a solid substance, if appropriate dissolved in the water-soluble polymer, in the micro-throughflow channel, which for its part is then dissolved from the buffer reservoir or advantageously from the same water reservoir. Finally, by analogy with the previous steps, the preparation and feeding in of enzyme substrate solution takes place.

Chemical equilibriums and the rate of reaction of chemical or biochemical enzymatic reactions are subject to a strong temperature influence. For example, the partial pressures of the dissolved blood gases $O_2$ and $CO_2$ are dependent on temperature and, in the case of laboratory equipment, are therefore always measured at 37° C. With sensors based on silicon technology and microelectronic circuitry, it is now possible to measure and control the temperature of the sensor chip, and consequently also the temperature of the sample. A restriction in this respect was until now constituted by the fact that, although a silicon chip can be electrically heated up, for example by resistance heating, it cannot be electrically cooled. This is achieved by an advantageous development of the invention.

A further advantageous application possibility of the invention is the amplification of DNA/RNA (deoxyribonucleic acid/ribonucleic acid) samples by the exponential replication method with the so-called PCR (Polymer Chain Reaction), i.e. the polymerase chain reaction method. For this purpose, the sample fluid must be cycled 20 to 40 times between two temperatures, typically between 40° C. and 95° C. In the case of the prior art, the cooling process is speed-determining for this thermal cycling.

The latter problems can also be solved in a practical way by the invention: for a specific application, a particularly advantageous embodiment similar to the chip module of a chip card comes into consideration as the applicator.

In the case of the chip card module, the silicon chip is advantageously mounted on a gold-coated copper layer only approximately 50 µm thick. This is the middle metal zone of known chip card modules, which is not used for electrical contacting points in the card reader. This free zone can consequently be used in the card reader, which acts here equally as an evaluation device, for directly contacting a cooling element, for example a Peltier cooler, to the corresponding location of the chip card module. On account of the placement (50 µm thick metallic contact with respect to the chip), an efficient heat transfer is consequently possible, so that a defined temperature can be set very quickly, in particular also by cooling.

BRIEF DESCRIPTION OF THE DRAWINGS

These and other objects and advantages of the present invention will become more apparent and more readily appreciated from the following description of exemplary embodiments, taken in conjunction with the accompanying drawings of which.

DETAILED DESCRIPTION OF THE PREFERRED EMBODIMENT

Figure 1:
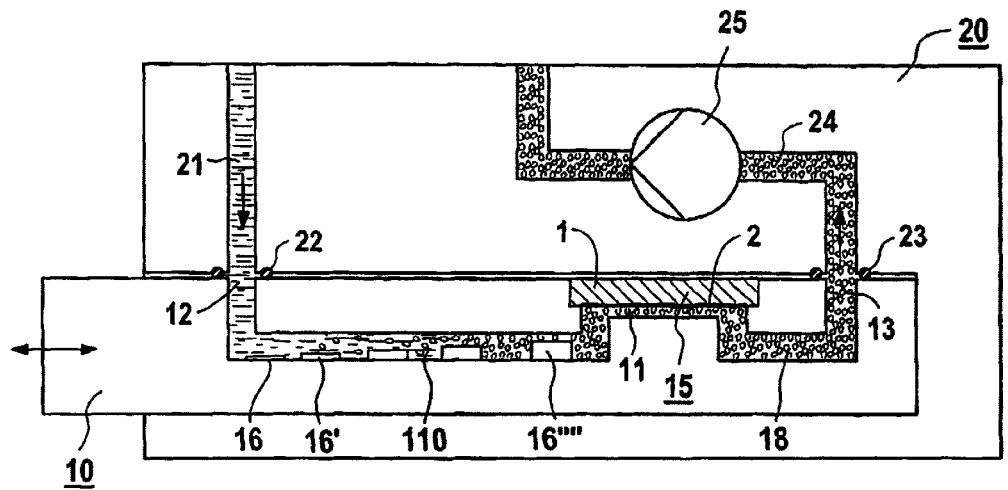
FIGS. 1 to 3 are cross-sectional views of three different embodiments of a so-called diagnosis kit an applicator and a reader.

Reference will now be made in detail to the preferred embodiments of the present invention, examples of which are illustrated in the accompanying drawings, wherein like reference numerals refer to like elements throughout.

Figure 6:
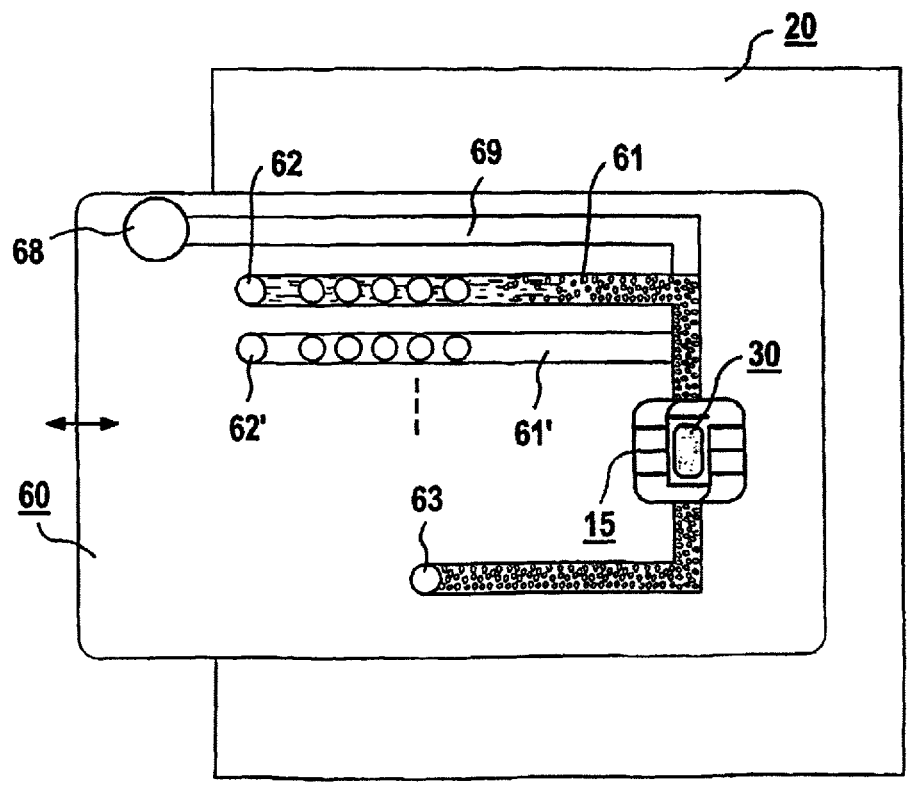
FIG. 6 is a plan view of a sample and multichannel reagent feed with a distribution system in the reader and FIGS. 7 and 8 are plan views of a multichannel reagent feed, modified with respect FIG. 6, by displacing the chip card into two positions.
Figure 7:
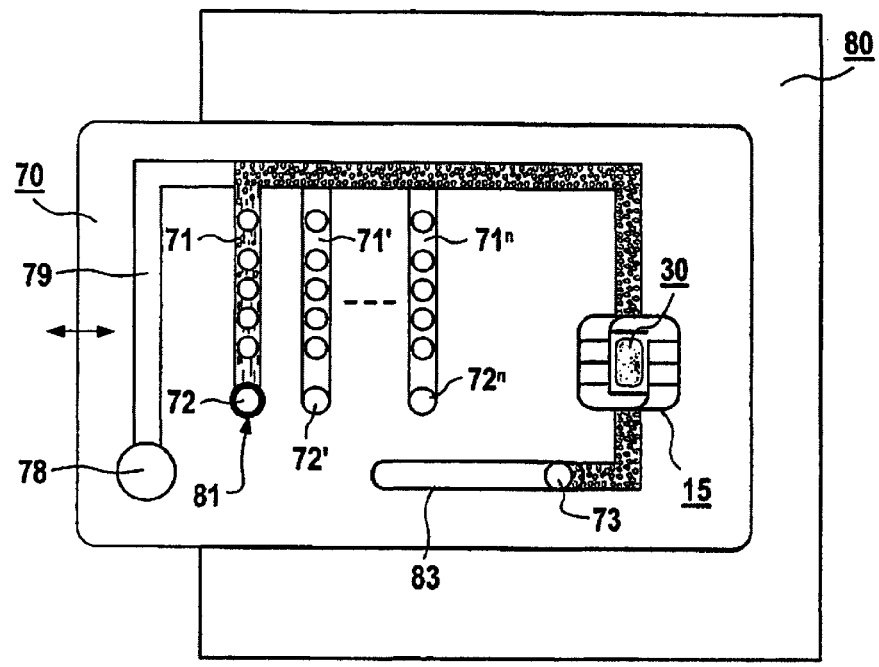

In FIGS. 1 to 4, an applicator with a sensor module is designated throughout by 10, while in FIGS. 6 and 7 a modified applicator is designated by 60 or 70. For measuring, such an applicator 10, 60 or 70 is pushed into a reader 20 or 80.

Figure 2:
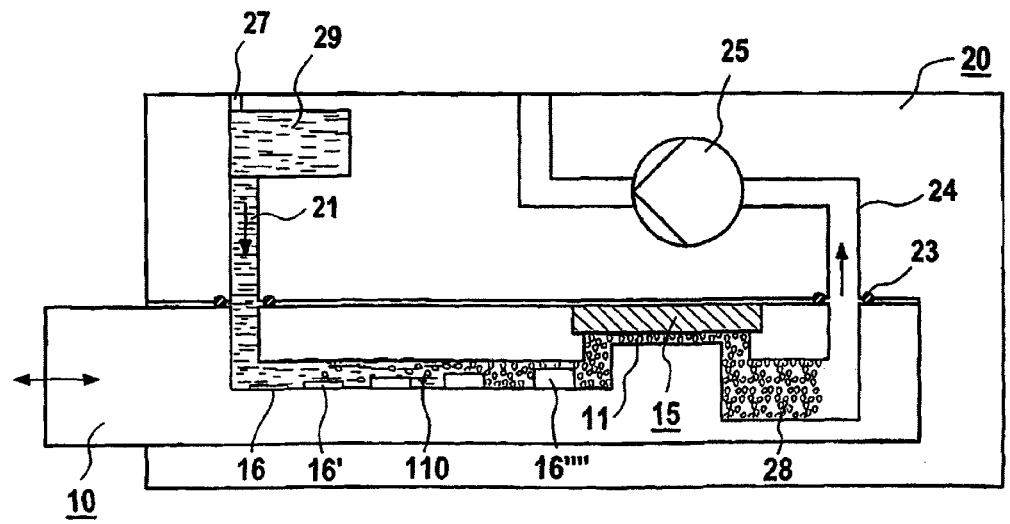
Figure 3:
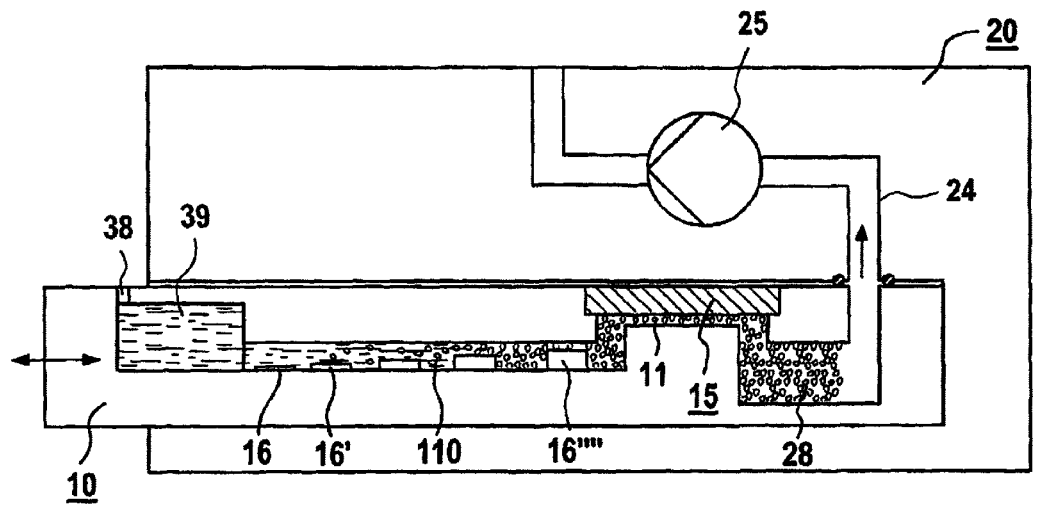

In FIGS. 1 to 3, a sensor module 15, for example a silicon chip 1 with a sensitive area 2, has been introduced into the applicator 10, encapsulated and electrically contacted on a carrier. Such a sensor module is the subject, inter alia, of a corresponding patent application with the same priority. On the sensor module 15 there is a microfluidic channel 11, to which a channel 110, in which reagents or adjuvants 16, 16', . . . , 16''' are arranged, leads from an inlet 12 with a valve arrangement/seal. Behind the sensor module 15, i.e. after the measurement, the substance is taken up by an outlet channel 18.

The reader 20 has in the housing fluid channels 21, with water, for example, being brought into the applicator 10 in the first channel 21, from a solvent store outside or inside the device, via a seal 22. The used measuring fluid is pumped via the seal of the outlet 23 by a pump 25 to a waste container, not represented in FIG. 1, inside or outside the reader.

The arrangement according to FIG. 2 corresponds substantially to FIG. 1, with the modifications that a solvent reservoir 29 has been placed in the second housing of the reader and, after the sensor module 15, the microfluid channel 11 has a widening or lengthening as a collecting container 28 for the purpose of taking up used solution or analyzed sample. If appropriate, such a widening is adequate as a reservoir for waste. In this case, only air is passed into the reader by the pump 25 via the outlet 13 with valves or seals 13 or 23.

In a corresponding development, the applicator 10 according to FIG. 3 includes a separate container 39 for a solvent store, i.e. for water. The water feed from the external device 20 is not necessary here. It is merely the case that the valve 12 from FIG. 1 is specifically formed as an air-admitting valve 38.

Figure 4:
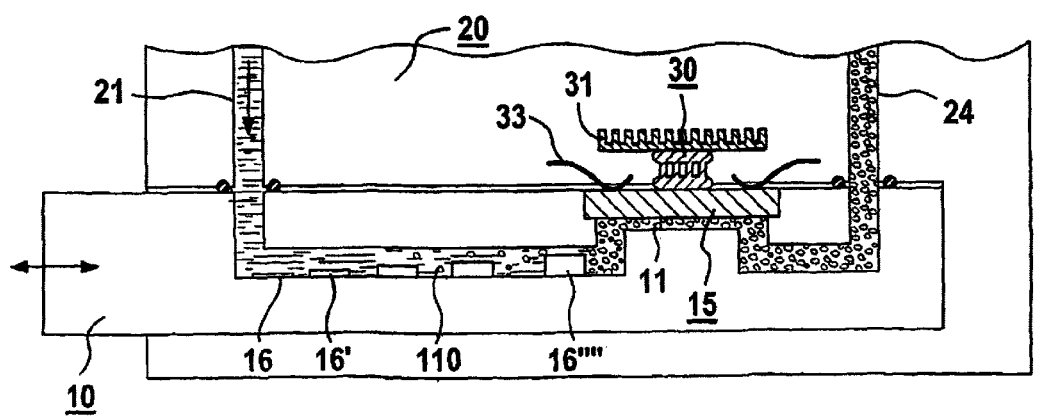
FIG. 4 is a sectional view of a reader with an integrated cooling element for direct thermal coupling to a chip-card contacting zone.

In FIG. 4, the applicator with the sensor module is formed substantially in a way corresponding to FIG. 1. Specifically in the reader, a heating and/or cooling element, for example a Peltier element 30, is arranged at the position of the sensor module 15 with the applicator pushed in. The Peltier element 30 has a cooling plate 31. With the Peltier element 30, effective and rapid cooling of the sensor module 15 to a defined temperature is possible.

This arrangement can preferably also be used for the amplification of DNA/RNA (deoxyribonucleic acid/ribonucleic acid) by the exponential replication method, the so-called PCR (Polymer Chain Reaction). For this purpose, the DNA/RNA sample and required reagents, such as for example nucleotide triphosphates, primer DNA/RNA and polymerase in buffer solution are fed to the sensitive area of the sensor chip via the microfluidic channels. The reaction space (space over the sensitive area of the chip with a height of up to several hundred μm), is then cycled approximately 20 to 40 times between two temperatures, typically between 40° C. and 95° C. In the case of this arrangement, the entire DNA/RNA replication process can be carried out in a few minutes.

Figure 5:
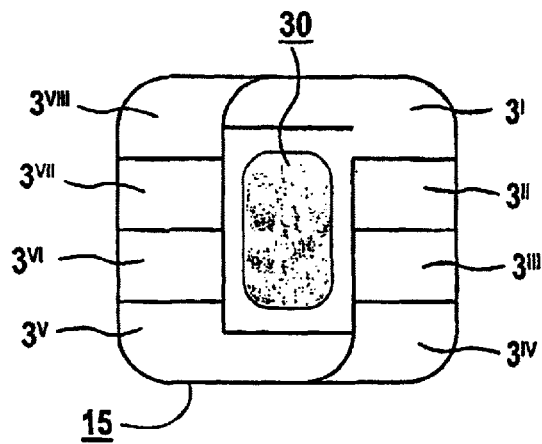
FIG. 5 is a plan view of the contacting zone of the module according to FIG. 4.

The operating principle of the chip module 15, and in particular of the actual sensor chip, is illustrated in FIG. 5. On the electrical contact side 3, i.e. the rear side, of the module 15 with the sensor chip 1, contacting zones $3^I, \ldots, 3^{VIII}$ can be seen as individual terminals, which correspond to the customary contacting points for chips which can be integrated into a card. On the sensitive side 2 of the chip 1, bonding pads run from the corners of the chip to the contacts of the contacting zones $3^I, \ldots 3^{VIII}$.

The latter arrangement is the subject of a parallel application with the same priority date (German patent application number 101 11 458.5-52 of 09.03.2001), to the disclosure of which reference is expressly made.

It is evident from FIG. 5, in the plan view, that for the case of chip card technology with a silicon chip and rear area contacts $3^I$ to $3^{VIII}$, as known from customary chip cards, the Peltier element 30 directly touches the effective area of the sensor on the rear side, and consequently brings about effective heat transfer.

Represented in FIG. 6, in the plan view, is a chip card 60 which has a sensor module 15 with a rear Peltier element 30 and electrical chip contacts 3' to $3^{VIII}$. There is a sample port 68 as a sample feed opening and also a sample channel 69 for feeding the sample to the sensor module 15. Also present are reagent channels with non-volatile reagents in a pre-measured amount. There is a first reagent channel 61, which is connected to a water inlet 62. Furthermore, there is a second reagent channel 61', which runs parallel to the first reagent channel 61 and, by contrast with the reagent channel 61, is not yet filled with solvent in the representation of FIG. 6, and consequently does not yet contain any reagent solution. The second reagent channel 61' can be connected to a second water inlet 62'. Further parallel-connected reagent channels 61" may be provided, with water inlets 62", which are respectively parallel-connected, so that altogether n reagent channels and n water inlets are present. After flowing past the sensor module 15, there is an outlet 63. In the reader 20 there is a water distribution system with valves.

Figure 8:
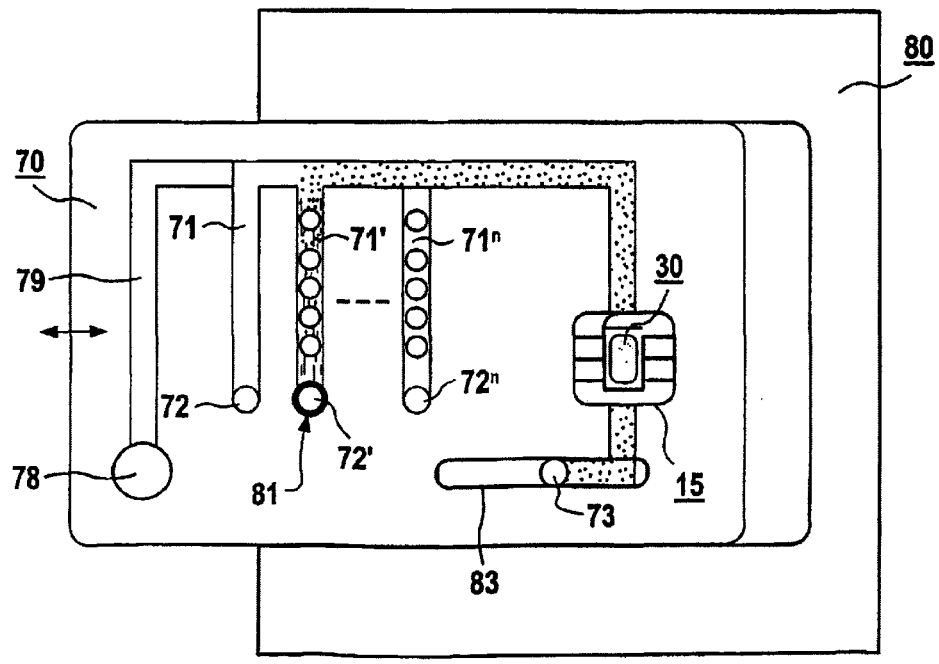

The operating principle of an arrangement modified with respect to the arrangement of FIG. 6 is illustrated on the basis of two subfigures 7 and 8. On the applicator 70 there are in turn a sample feed opening 78, as the sample port, and also a sample channel 79 for feeding the sample to the sensor module 15. Also present are reagent channels 71 to 71n' and an outlet 73. In the case of this arrangement, in the reader 80 there is a single inflow channel, which has a single inflow opening 81 and a single outflow opening 83. In the position illustrated in FIG. 7, the first reagent channel 71 is congruent with the inflow opening 81, while in the position illustrated in FIG. 8, the second reagent channel 71' is congruent with the inflow opening 81. The outlet opening 83 is in this case formed as a slit opening, so that in both positions of the applicator and also in further positions it is always possible for the outlet 73 to be toward the outlet 83 of the reader 80.

In the case of the arrangements described, it is important for the microfluidic analysis/diagnosis system that it is possible to store each time a defined amount of at least one reagent, to store the reagent in a stable form, to store the reagent as a pure and solid substance or to store the reagent in a dissolved or mixed form in a further substance (adjuvant). Such an adjuvant may be solid or liquid. A solid adjuvant may be, for example, a water-soluble polymer such as polyvinyl alcohol. The adjuvant may serve the purpose of diluting reagent (for example when using enzymes which are to be used in very small amounts) and/or placing them in a container in such a way that they are geometrically defined and have good adhesion.

Irrespective of the representation in the drawings, the applicator has a defined geometry as a plastic housing. In the plastic housing are micro-channels with a cross section of for example 1 mm×0.1 mm and a length of several mm, which form a fluid system. Reagent dissolved in the adjuvant may be placed in a defined quantitative gradient along a micro-channel. The plastic housing may contain a defined store of solvent. Furthermore, the plastic housing may contain a defined empty volume for the disposal of waste.

In the case of all the examples, the plastic housing as the applicator in combination with the reader and the suitable operating mode allow reagent and solvent to be brought together. The plastic housing is connected by at least one micro-channel to a reader. The reader contains a storage container in which there is, in the simplest case, water, adequate for a number of analyses. The reader may contain a container for the disposal of the waste from a number of analyses and also contains means for conveying the solvent through the micro-channels to the sensor module and further to the waste container in the plastic housing or in the reader. The solvent, no matter from which store, is passed over the geometrically placed reagent-adjuvant mixture in such a way that a defined solution can be produced, under some circumstances by the solvent remaining for a time over the solid substance, pumping forward and back, heating or the like.

In the way described, even uncritical reagent solutions, such as buffer solutions or the like, can be generated in the analysis kit. Although stable buffer solutions could also be fed in from a storage container in the reader, with the applicator removed the interfaces between the reader and the applicator are susceptible to evaporation of the solvent and consequently precipitation of solid substance (for example salt) and soiling/encrusting of the fluidic interfaces. This is not to be feared in the case in which pure solvent is stored in the reader. What is more, this method allows a number of reagent solutions to be realized in a simple way by arranging the reagent channels from just one solvent reservoir in parallel.

A special case exists when providing reagent for sensors of dissolved gases, for example in the case of sensors for determining the blood gases oxygen and carbon dioxide. Here, the sensors must be calibrated with media, for example solutions, which have a defined concentration of the respective gases.

In the case of blood-gas sensors, which for example for so-called "point of care diagnostics" have to be calibrated once before they are used a single time, the sensors for $pO_2$ and $pCO_2$ have to be brought into contact with buffer solutions of known $pO_2$ and $pCO_2$ values. While previously a single solution with known $pO_2$ and $pCO_2$ values, already prepared during the production of the module, was filled into a small gastight bag and fitted into the diagnosis module, now the calibration can be performed as desired, in particular as a two-point calibration.

This consequently provides an analysis device which can be used in a variety of ways in biochemical analytics, for example for use in medical diagnostics, forensics, for food monitoring and for environmental measuring technology. The decentralized use of the applicator and reader allows time-saving low-cost examination on the spot, in particular in clinics and doctors' own practices, of for example blood, liquor, saliva and smears, for example for viruses of infectious diseases. This may include, if necessary, not only simple typing of the germs, but also the determination of any resistances to antibiotics, which significantly improves the quality of the therapy and consequently can reduce the duration and cost of the illness. Apart from the diagnosis of infectious diseases, the diagnosis system is for example also suitable in medicine for blood gas/blood electrolyte analysis, for therapy control, for early detection of cancer and for the determination of genetic predispositions.

The invention has been described in detail with particular reference to preferred embodiments thereof and examples, but it will be understood that variations and modifications can be effected within the spirit and scope of the invention.

The invention claimed is:

1. An analysis device for use in biochemical analytics, comprising:
   an applicator for decentralized use, including
      a first housing providing at least one channel for a microfluidic system,
      at least one reagent in a pre-portioned amount included within the at least one channel of the first housing, the at least one reagent being a solid, non-volatile substance, and
      a chip module provided adjacent to the first housing, the chip module having a sensitive side that is microfluidically accessible to the at least one channel and an electrical contact side opposite the sensitive side;
   a second housing, removably connected to said first housing and said chip module, to receive signals from the chip module to form a measuring and analysis system; and
   a channel configured to provide a solvent to dissolve the pre-portioned amount of the at least one reagent and form a solution within the at least one channel of the first housing to be fed to the sensitive side of the chip module when the first housing is inserted into the second housing.

2. The analysis device as claimed in claim 1, wherein the electrical contact side of the chip module has an electrical contacting zone for feeding in and tapping electrical signals.

3. The analysis device as claimed in claim 1, wherein said channel includes a solvent reservoir and said second housing provides the solvent reservoir coupled to the channel for the microfluidic system.

4. The analysis device as claimed in claim 1, wherein the channel includes a solvent reservoir and the solvent reservoir is arranged in said applicator.

5. The analysis device as claimed in claim 1, wherein one defined quantity of each of different reagents is present in said applicator.

6. The analysis device as claimed in claim 1, wherein the at least one reagent is in a stable form.

7. The analysis device as claimed in claim 1, wherein the at least one reagent is a pure solid substance.

8. The analysis device as claimed in claim 1, wherein the at least one reagent is in one of a dissolved and mixed form in an adjuvant.

9. The analysis device as claimed in claim 8, wherein the adjuvant is one of solid and liquid.

10. The analysis device as claimed in claim 9, wherein the adjuvant is a water-soluble polymer.

11. The analysis device as claimed in claim 8, wherein the adjuvant dilutes the at least one reagent and transports the at least one reagent to a container in said applicator to provide geometric definition and good adhesion.

12. The analysis device as claimed in claim 11, wherein the container in said applicator further includes a microchannel with a cross section and a length.

13. The analysis device as claimed in claim 12, wherein the at least one reagent diluted by the adjuvant is arranged in a quantitative gradient along the microchannel.

14. The analysis device as claimed in claim 1, wherein said applicator comprises a plastic card provided with microfluidic components.

15. The analysis device as claimed in claim 14, wherein the plastic card is a chip card.

16. The analysis device as claimed in claim 15, wherein said second housing comprises a reader, into which said applicator is inserted.

17. The analysis device as claimed in claim 16, wherein when said applicator is inserted into the reader, the at least one reagent and the solvent are brought together.

18. The analysis device as claimed in claim 17, wherein at least one continuous fluid channel is formed between said applicator and the reader via at least one seal provided between the applicator and the reader.

19. The analysis device as claimed in claim 18, wherein the channel configured to provide the solvent includes a solvent reservoir and the solvent reservoir is provided in the reader and holds water for multiple analyses.

20. The analysis device as claimed in claim 18, further comprising a container to receive waste sample material and used reagents.

21. The analysis device as claimed in claim 20, wherein the container is arranged in one of the first housing of said applicator and the second housing of the reader.

22. The analysis device as claimed in claim 21, wherein the reader includes the channel configured to provide the solvent and conveys the solvent through the at least one continuous fluid channel to the sensor module and then to said container.

23. The analysis device as claimed in claim 22, wherein the at least one continuous fluid channel causes the solvent to pass over a geometrically shaped reagent-adjuvant mixture to produce the solution.

24. The analysis device as claimed in claim 23, further comprising means for keeping the solvent at a predetermined solvent temperature.

25. The analysis device as claimed in claim 24, further comprising temperature maintenance means for maintaining a predetermined temperature at the chip module.

26. The analysis device as claimed in claim 25, wherein said temperature maintenance means comprises a Peltier element in the second housing exerting a thermostatically controlling effect to cool the chip module.

27. The analysis device as claimed in claim 26, wherein the biochemical analytics is DNA analysis.

28. The analysis device as claimed in claim 26, wherein the biochemical analytics uses a Polymer Chain Reaction and said analysis device speeds cooling during the Polymer Chain Reaction.

29. The analysis device as claimed in claim 24, wherein the biochemical analytics is food monitoring.

30. The analysis device as claimed in claim 24, wherein the biochemical analytics is environmental measuring.

31. The analysis device as claimed in claim 24, wherein the biochemical analytics is forensics.

32. The analysis device as claimed in claim 24, wherein the biochemical analytics is medical diagnostics.

33. The analysis device as claimed in claim 32, wherein the biochemical analytics is blood gas/blood electrolyte analysis.

34. The analysis device as claimed in claim 32, wherein the biochemical analytics is diagnosis of infectious diseases.

35. The analysis device as claimed in claim 32, wherein the biochemical analytics is therapy control.

36. The analysis device as claimed in claim 32, wherein the biochemical analytics is early detection of diseases.

* * * * *